(12) United States Patent
Code et al.

(10) Patent No.: US 8,679,515 B2
(45) Date of Patent: Mar. 25, 2014

(54) ACTIVATED CARBON ASSOCIATED WITH ALKALINE OR ALKALI IODIDE

(75) Inventors: Kenneth R. Code, Spruce Grove (CA); Joseph Provenzano, Huntington Beach, CA (US)

(73) Assignee: Biolargo Life Technologies, Inc., Irvine, CA (US)

( * ) Notice: Subject to any disclaimer, the term of this patent is extended or adjusted under 35 U.S.C. 154(b) by 0 days.

(21) Appl. No.: 13/475,102

(22) Filed: May 18, 2012

(65) Prior Publication Data
US 2012/0263801 A1    Oct. 18, 2012

Related U.S. Application Data

(63) Continuation-in-part of application No. 12/009,586, filed on Jan. 18, 2008, now Pat. No. 8,226,964.

(60) Provisional application No. 61/490,448, filed on May 26, 2011.

(51) Int. Cl.
*A01N 25/08*    (2006.01)

(52) U.S. Cl.
USPC ........... 424/405; 205/742; 205/747; 205/748; 205/749; 205/750; 210/348; 422/4; 422/22; 422/26; 422/27; 422/30; 424/125; 424/404; 424/406; 424/407; 424/409; 424/411; 424/417; 424/421; 424/667; 424/670; 588/204; 588/206; 588/222; 588/225; 588/226

(58) Field of Classification Search
USPC ................. 424/125, 405, 409, 420, 667, 670; 205/742, 747, 748, 751, 753, 768; 210/348, 748, 749, 753; 422/4, 22, 26, 422/27, 30, 31, 37; 588/204, 206, 222, 225, 588/226, 227, 228
See application file for complete search history.

(56) References Cited

U.S. PATENT DOCUMENTS

| | | | | |
|---|---|---|---|---|
| 2,123,092 | A | * | 7/1938 | Behrman ................... 210/794 |
| 3,891,741 | A | * | 6/1975 | Carlin et al. .................. 205/43 |
| 6,638,347 | B2 | | 10/2003 | El-Shoubary et al. |
| 6,953,494 | B2 | | 10/2005 | Nelson, Jr. |
| 7,442,352 | B2 | | 10/2008 | Lu et al. |
| 7,736,611 | B2 | | 6/2010 | Norberg et al. |
| 7,850,764 | B2 | | 12/2010 | DeBerry |
| 2010/0230359 | A1 | * | 9/2010 | Whitehead et al. .......... 210/679 |
| 2013/0032529 | A1 | * | 2/2013 | Hassler .................. 210/497.01 |

OTHER PUBLICATIONS

Prominent Systems, Inc., Impregnation Series, Website: http://www.prominentinc.com/cbac_impregnated_ki_nai.html, City of Industry, California, Copyright 2002-2009 Prominent Systems, Inc. printed on May 18, 2012.

* cited by examiner

*Primary Examiner* — Neil Levy
(74) *Attorney, Agent, or Firm* — Mark A. Litman & Associates, P.A.

(57) ABSTRACT

Contaminants are filtered from a fluid flow stream and the filter is regenerated by a process including steps of:
  providing a filter material comprising both carbon and potassium iodide;
  passing a contaminated fluid stream in contact with the filter material;
  adsorbing contaminants from the fluid stream onto surfaces in the filter material;
  passing an electric current through the filter material with adsorbed contaminant thereon;
  disassociating contaminant from the surfaces of the filter material; and
  removing disassociated contaminant from the filter material by carrying away the disassociated contaminant in a fluid flow mass.
Separately, a stable, active iodine solution is also provided for numerous deodorizing and disinfecting applications.

16 Claims, 1 Drawing Sheet

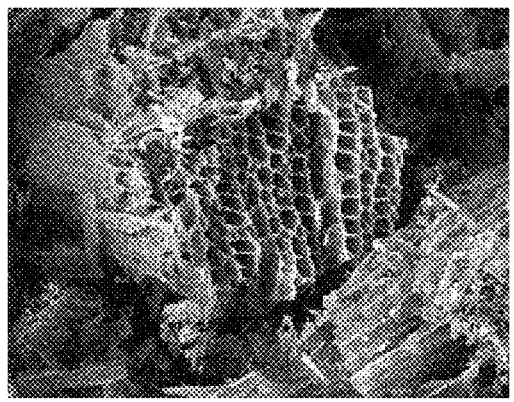

ACTIVATED CARBON ASSOCIATED WITH ALKALINE OR ALKALI IODIDE

RELATED APPLICATIONS DATA

This application claims priority as a continuation-in-part application under 35 U.S.C. 120 from U.S. patent application Ser. No. 12/009,586 filed 28 Jan. 2010.

BACKGROUND OF THE INVENTION

1. Field of the Invention

The present invention relates to the field of carbon filters and slurries, particularly activated carbon filters and slurries and the regeneration of used or spent activated carbon after use as a filter, precipitator or biologic reactor. Concentrated and active stable solutions of iodine are also described.

2. Background of the Art

Activated carbon, also called activated charcoal or activated coal is a form of carbon that has been processed to make it extremely porous and thus to have a very large surface area available for adsorption or chemical reactions. The carbon may be provided by many different processes and in many of the various forms of carbon available, such as powdered carbon, expanded carbon, graphite, expanded graphite and the like.

The word activated in the name is sometimes replaced with active. Due to its high degree of microporosity, just 1 gram of activated carbon has a surface area in excess of 500 $m^2$ (about one tenth the size of an American football field), as determined typically by nitrogen gas adsorption. Sufficient activation for useful applications may come solely from the high surface area, though further chemical treatment often enhances the adsorbing properties of the material. Activated carbon is usually derived from charcoal.

Activated carbon is carbon produced from carbonaceous source materials such as, by way of non-limiting examples, nutshells, peat, wood, coir, lignite, coal and petroleum pitch. It can be produced by one of the following non-limiting processes:

1. Physical reactivation: The precursor is developed into activated carbons using gases. This is generally done by using one or a combination of the following processes:
    Carbonization: Material with carbon content is pyrolyzed at temperatures in the range 600-900° C., in absence of oxygen (usually in inert atmosphere with gases like argon or nitrogen)
    Activation/Oxidation: Raw material or carbonized material is exposed to oxidizing atmospheres (carbon monoxide, oxygen, or steam) at temperatures above 250° C., usually in the temperature range of 600-1200° C.
2. Chemical activation: Prior to carbonization, the raw material is impregnated with certain chemicals. The chemical is typically an acid, strong base, or a salt (phosphoric acid, potassium hydroxide, sodium hydroxide, zinc chloride, respectively). Then, the raw material is carbonized at lower temperatures (450-900° C.). It is believed that the carbonization/activation step proceeds simultaneously with the chemical activation. Chemical activation is preferred over physical activation owing to the lower temperatures and shorter time needed for activating material.

Activated carbons are complex products which are difficult to classify on the basis of their behavior, surface characteristics and preparation methods. However, some broad classification is made for general purpose based on their physical characteristics. They may be formally or informally characterized according to properties, method of production, morphology and/or other factors.

One form of activated carbon is known as powdered activated carbon (PAC). Activated charcoal under bright field illumination on a light microscope displays a fractal-like shape of the particles hinting at their enormous surface area. Each particle despite being only around 0.1 mm wide, has a surface area of several square meters.

Traditionally, active carbons are made in particulate form as powders or fine granules less than 1.0 mm in size with an average diameter between 0.15 and 0.25 mm. Thus they present a large surface to volume ratio with a small diffusion distance. PAC is made up of crushed or ground carbon particles, 95-100% of which will pass through a designated mesh sieve or sieve. Granular activated carbon is defined as the activated carbon being retained on a 50-mesh sieve (0.297 mm) and PAC material as finer material, while ASTM classifies particle sizes corresponding to an 80-mesh sieve (0.177 mm) and smaller as PAC. PAC is not commonly used in a dedicated vessel, owing to the high head loss that would occur. PAC is generally added directly to other process units, such as raw water intakes, rapid mix basins, clarifiers, and gravity filters.

Granular activated carbon is another form of activated carbon that has a relatively larger particle size compared to powdered activated carbon and consequently, presents a smaller external surface. Diffusion of the adsorbate is thus an important factor. These carbons are therefore preferred for all adsorption of gases and vapors as their rate of diffusion are faster. Granulated carbons are used for water treatment, deodorization and separation of components of flow system. GAC can be either in the granular form or extruded. GAC is designated by sizes such as 8×20, 20×40, or 8×30 for liquid phase applications and 4×6, 4×8 or 4×10 for vapor phase applications. A 20×40 carbon is made of particles that will pass through a U.S. Standard Mesh Size No. 20 sieve (0.84 mm) (generally specified as 85% passing) but be retained on a U.S. Standard Mesh Size No. 40 sieve (0.42 mm) (generally specified as 95% retained). AWWA (1992) B604 uses the 50-mesh sieve (0.297 mm) as the minimum GAC size. The most popular aqueous phase carbons are the 12×40 and 8×30 sizes because they have a good balance of size, surface area, and head loss characteristics.

Extruded activated carbon is another form that combines powdered activated carbon with a binder, which are fused together and extruded into a cylindrical shaped activated carbon block with diameters from 0.8 to 130 mm. These are mainly used for gas phase applications because of their low pressure drop, high mechanical strength and low dust content.

Impregnated carbon is a porous carbon containing several types of inorganic impregnant such as iodine, silver, cations such as Al, Mn, Zn, Fe, Li, Ca have also been prepared for specific application in air pollution control especially in museums and galleries. Due to antimicrobial/antiseptic properties, silver loaded activated carbon is used as an adsorbent for purification of domestic water. Drinking water can be obtained from natural water by treating the natural water with a mixture of activated carbon and $Al(OH)_3$, a flocculating agent. Impregnated carbons are also used for the adsorption of $H_2S$ and thiols. Adsorption rates for $H_2S$ as high as 50% by weight have been reported.

Activated carbon is also available in special forms such as cloths and fibers. The "carbon cloth" for instance is used in personnel protection for the military.

A gram of activated carbon can have a surface area in excess of 500 $m^2$, with 1500 $m^2$ being readily achievable.

Carbon aerogels, while more expensive, have even higher surface areas, and are used in special applications. FIG. 1 shows Activated carbon, as viewed by an electron microscope.

Under an electron microscope, the high surface-area structures of activated carbon are revealed. Individual particles are intensely convoluted and display various kinds of porosity; there may be many areas where flat surfaces of graphite-like material run parallel to each other, separated by only a few nanometers or so. These micropores provide superb conditions for adsorption to occur, since adsorbing material can interact with many surfaces simultaneously. Tests of adsorption behavior are usually done with nitrogen gas at 77 K under high vacuum), but in everyday terms activated carbon is perfectly capable of producing the equivalent, by adsorption from its environment, liquid water from steam at 100° C. and a pressure of 1/10,000 of an atmosphere.

Physically, activated carbon binds materials by van der Waals force or London dispersion force. Activated carbon does not bind well to certain chemicals, including alcohols, glycols, strong acids and bases, metals and most inorganics, such as lithium, sodium, iron, lead, arsenic, fluorine, and boric acid. Activated carbon does adsorb iodine very well and in fact the iodine number, mg/g, (ASTM D28 Standard Method test) is used as an indication of total surface area. Ammonia adsorption on activated carbon is both temperature and concentration dependent, directly, in aqueous liquids.

Carbon monoxide is not well absorbed by activated carbon. This should be of particular concern to those using the material in filters for respirators, fume hoods or other gas control systems as the gas is undetectable to the human senses, toxic to metabolism and neurotoxic.

Activated carbon can be used as a substrate for the application of various chemicals which improve the adsorptive capacity for some inorganic (and problematic organic) compounds such as hydrogen sulfide ($H_2S$), ammonia ($NH_3$), formaldehyde (HCOH), radioisotopes iodine-131($^{131}I$) and mercury (Hg). This property is known as chemisorption.

Iodine Number

Many carbons preferentially adsorb small molecules. Iodine number is the most fundamental parameter used to characterize activated carbon performance. It is a measure of activity level (higher number indicates higher degree of activation), often reported in mg/g (typical range 500-1200 mg/g). It is a measure of the micropore content of the activated carbon (0 to 20 Å, or up to 2 nm) by adsorption of iodine from solution. It is equivalent to surface area of carbon between 900 $m^2/g$ and 1100 $m^2/g$. It is the standard measure for liquid phase applications.

Iodine number is defined as the milligrams of iodine adsorbed by one gram of a material such as carbon, organic materials (such as oils, lipids, hydrocarbons, carbohydrates, etc.) when the iodine concentration in the residual filtrate is 0.02 normal. Basically, iodine number is a measure of the iodine adsorbed in the pores and, as such, is an indication of the pore volume available in the activated carbon of interest. Typically, water treatment carbons have iodine numbers ranging from 600 to 1100. Frequently, this parameter is used to determine the degree of exhaustion of a carbon in use. However, this practice should be viewed with caution as chemical interactions with the adsorbate may affect the iodine uptake giving false results. Thus, the use of iodine number as a measure of the degree of exhaustion of a carbon bed can only be recommended if it has been shown to be free of chemical interactions with adsorbates and if an experimental correlation between iodine number and the degree of exhaustion has been determined for the particular application. Although carbon is primarily described herein, any other surface on a material (porous or not) may also be used as long as it can sustain or provide an iodine number of at least 100 mg/g. Silicone materials, polymers, composites, coated substrates (such as carbon coated, or graphite coated substrates) and the like are examples thereof. These materials are preferably porous or microporous to allow high surface areas per volume of material.

Dechlorination

Some carbons are evaluated based on the dechlorination half-value length, which measures the chlorine-removal efficiency of activated carbon. The dechlorination half-value length is the depth of carbon required to reduce the chlorine level of a flowing stream from 5 ppm to 3.5 ppm. A lower half-value length indicates superior performance.

Ash Content

Ash content reduces the overall activity of activated carbon. It reduces the efficiency of reactivation. The metal oxides ($Fe_2O_3$) can leach out of activated carbon resulting in discoloration. Acid/water soluble ash content is more significant than total ash content. Soluble ash content can be very important for aquarists, as ferric oxide can promote algal growths. A carbon with a low soluble ash content should be used for marine, freshwater fish and reef tanks to avoid heavy metal poisoning and excess plant/algal growth.

Carbon Tetrachloride Activity

Measurement of the porosity of an activated carbon by the adsorption of saturated carbon tetrachloride vapor.

Particle Size Distribution

The finer the particle size of an activated carbon, the better the access to the surface area and the faster the rate of adsorption kinetics. In vapor phase systems this needs to be considered against pressure drop, which will affect energy cost. Careful consideration of particle size distribution can provide significant operating benefits.

The most commonly encountered form of chemisorption in industry, occurs when a solid catalyst interacts with a gaseous feedstock, the reactant/s. The adsorption of reactant/s to the catalyst surface creates a chemical bond, altering the electron density around the reactant molecule and allowing it to undergo reactions that would not normally be available to it.

Carbon adsorption has numerous applications in removing pollutants from air or water streams both in the field and in industrial processes such as:

Spill cleanup
Groundwater remediation
Drinking water filtration
Air purification
Volatile organic compounds capture from painting, dry cleaning, gasoline dispensing operations, and other processes.

Activated charcoal is also used for the measurement of radon concentration in air.

Activated carbon is also used as growth media in biologic methods of water and wastewater treatment.

Research is being done testing various activated carbons' ability to store natural gas and hydrogen gas. The porous material acts like a sponge for different types of gasses. The gas is attracted to the carbon material via Van der Waals forces. Some carbons have been able to achieve bonding energies of 5-10 kJ per mol. The gas may then be desorbed when subjected to higher temperatures and either combusted to do work or in the case of hydrogen gas extracted for use in a hydrogen fuel cell. Gas storage in activated carbons is an appealing gas storage method because the gas can be stored in a low pressure, low mass, low volume environment that would be much more feasible than bulky on board compression tanks in vehicles.

Filters with activated carbon are usually used in compressed air and gas purification to remove oil vapors, odors, and other hydrocarbons from the air. The most common designs use a 1 stage or 2 stage filtration principle in which activated carbon is embedded inside the filter media. Activated charcoal is also used in spacesuit Primary Life Support Systems. Activated charcoal filters are used to retain radioactive gases from a nuclear boiling water reactor turbine condenser. The air vacuumed from the condenser contains traces of radioactive gases. The large charcoal beds adsorb these gases and retain them while they rapidly decay to non-radioactive solid species. The solids are trapped in the charcoal particles, while the filtered air passes through.

Activated carbon is commonly used to purify homemade non-dangerous chemicals such as sodium acetate. Activated carbon, often impregnated with iodine or sulfur, is widely used to trap mercury emissions from coal-fired power stations, medical incinerators, and from natural gas at the wellhead. This carbon is a specialty product costing more than US$4.00 per kg. However, it is often not recycled, if it can be.

The regeneration of activated carbons involves restoring the adsorptive capacity of saturated activated carbon by desorbing adsorbed contaminants on the activated carbon surface. This has been practiced with a number of available techniques. The most common regeneration technique employed in industrial processes is thermal regeneration. The thermal regeneration process generally follows three steps:

Adsorbent drying at approximately 105° C.

High temperature desorption and decomposition (500-900° C.) under an inert atmosphere Residual organic gasification by an oxidizing gas (steam or carbon dioxide) at elevated temperatures (800° C.)

The heat treatment stage utilizes the exothermic nature of adsorption and results in desorption, partial cracking and polymerization of the adsorbed organics. The final step aims to remove charred organic residue formed in the porous structure in the previous stage and re-expose the porous carbon structure regenerating its original surface characteristics. After treatment the adsorption column can be reused. Per adsorption-thermal regeneration cycle between 5-15 wt % of the carbon bed is burnt off resulting in a loss of adsorptive capacity. Thermal regeneration is a high energy process due to the high required temperatures making it both an energetically and commercially expensive process. Plants that rely on thermal regeneration of activated carbon have to be of a certain size before it is economically viable to have regeneration facilities onsite. As a result it is common for smaller waste treatment sites to ship their activated carbon cores to a specialized facility for regeneration, increasing the process' already significant carbon footprint http://www.prominentinc.com/cbac_impregnated_ki_nai.html discloses KI impregnated activated carbon.

KI/Potassium Iodide Impregnated Coal Based Activated Carbon.

It is effective for the desulphurization of gases and the removal of acidic contaminants such as hydrogen sulfide, hydrogen chloride, and mercaptans. The percentage of potassium iodine can be varied upon request.

| | Unit | | Available Products Range | Remarks |
|---|---|---|---|---|
| Mesh Size | US Sieve | | GAC: 4 × 6/ 4 × 8/4 × 10/ 8 × 20 | or as required |
| Diameter | mm | | PAC: 1.5/3.0/4.0 | or as required |
| Iodine | mg/g | Minimum | 1000 | or as required |
| CCL4/CTC | % | Minimum | 60/65/70/75 | or as required |
| KI Impregnation | % | Minimum | 2/3/5 | or as required |
| $H_2S$ Break Through Capacity | g/cc | Minimum | 0.14 | or as required |
| Apparent Density | g/cc | | 0.50-0.66 | or as required |
| Hardness | % | Minimum | 90/95 | or as required |
| Moisture | % | Maximum | 15 | or as required |

Chemical and Engineering News, Apr. 10, 2010, Volume 88, No. 6 "Wastewater Treatment," Melody Voith, discloses a process for cleaning wastewater from paper plant manufacturing sites by adsorption of organic chemical wastes by passing low-voltage electric current through a graphite-based filter to cause electrochemical oxidation of organic on the particles. The carbon particles are first mixed with the wastewater top absorb the organic wastes. The current directly oxidizes the organic materials.

SUMMARY OF THE INVENTION

A carbon filter is activated by intimate, internal association with iodine and/or potassium iodide (KI). This material will be referred to herein as IAC (for Iodine (iodide) activated carbon. Spent or used IAC is saturated in an aqueous or alcoholic liquid while a current (e.g., DC or pulsed current) is passed through the spent IAC. The current both regenerates the IAC and oxidizes these contaminants. It regenerates the activity in the IAC by overcoming the forces binding the adsorbed materials to the IAC permitting the liquid supports to carry away the released formerly filtered and retained materials. As the adsorbed or absorbed materials filtered from either a gaseous or liquid medium are primarily associated with the activated carbon medium (the IAC) through electrical forces, as opposed to covalent bonding, application of current can be highly effective in freeing material bound to the IAC. The current also causes free iodine to be emitted from the KI and over the KI, and the iodine system oxidizes the adsorbed pollutants/contaminants. Rather than a direct electrochemical oxidation that must be tailored for each pollutant, the present system allows a single voltage to release the iodine which can then address any pollutant. The carbon may be reactivated, regenerated by adding additional KI into the carbon, as by passing a solution through the filter material, with adsorption of the KI molecules, with or without drying of the reactivating solution. In addition, the applied voltage and current may be optimized to yield only oxides as reaction products through reactions with autogenerated iodine pentoxides and other oxidative moieties, thus preserving the initial charge of iodide within the activated carbon.

Additionally, a stable acidified iodine ($I_2$) solution is disclosed.

U.S. Pat. No. 7,850,764 (DeBerry) describes removal of contaminants from vapor streams and incidentally discloses regeneration of the filter media by heating the used activated carbon, especially to release bound mercury or by using a complexing agent to reduce or oxidize the bound mercury and make it available for removal.

U.S. Pat. No. 7,736,611 (Norberg) discloses filter materials that are regenerated by heating or vapor flushing, including activated carbon filters.

U.S. Pat. No. 7,442,352 (Lu) discloses uses for removing contaminants using activated carbon and regenerating the activated carbon by thermal degassing or washing out of the gases.

U.S. Pat. No. 6,953,494 (Nelson) teaches the use of bromine gas in activated carbon to improve its ability to adsorb mercury from combustion emission.

U.S. Pat. No. 6,638,347 (El-Shoubary) discloses carbon-based, adsorption powder containing an effective amount of cupric chloride suitable for removing mercury from a high temperature, high moisture gas stream, wherein the effective amount of cupric chloride ranges from about 1 to about 45 wt percent. Additional additives, such as potassium permanganate, calcium hydroxide, potassium iodide and sulfur, may be added to the powder to enhance the removal of mercury from the gas stream.

All references cited herein are incorporated by reference in their entireties.

BRIEF DESCRIPTION OF THE FIGURES

FIG. 1 is a photomicrograph of internal structure of a porous carbon filter material.

DETAILED DESCRIPTION OF THE INVENTION

Carbon filters and especially activated carbon filters are capable of removing contaminants from fluid media (aqueous or liquid media). Among the species of contaminants are selected from the group consisting essentially of basic, acidic and hydrocarbon species. Other contaminants may include metal, semimetals, and ionic species. Any material that can be temporarily adsorbed or adsorbed by activated carbon by electrical forces (including Van der Waals forces) should be capable of removal by treatment according to the technology described herein.

The present technology includes a method of filtering contaminants from a fluid stream by:

providing a filter material comprising both carbon and potassium iodide;

passing a contaminated fluid stream in contact with the filter material;

adsorbing contaminants from the fluid stream onto surfaces in the filter material;

passing an electric current through the filter material with adsorbed contaminant thereon;

disassociating contaminant from the surfaces of the filter material; and removing disassociated contaminant from the filter material by carrying away the disassociated contaminant in a fluid flow mass.

The current causes the iodine to be emitted from the KI, and the iodine oxidizes the adsorbed pollutants/contaminants. Rather than a direct electrochemical oxidation that must be tailored for each pollutant, the present system allows a single voltage or current to release the iodine which can then address any pollutant. The carbon may be reactivated, regenerated by adding KI into the carbon, as by passing a solution through the filter material, causing adsorption of the KI molecules, with or without drying of the reactivating solution, or by voltage and current optimization to yield oxides instead of iodides as desired contaminant reaction products.

The filter material may be activated carbon and at least 0.05% by total weight of solids of potassium iodide. The potassium iodide may be intimately mixed throughout the activated carbon and/or the potassium iodide is distributed on at least some surfaces of the activated carbon. The electric current may be applied over a broad low to moderate range, such as being applied at voltages between 0.5 and 30V, preferably between 2.0 and 15 volts. The amperage may be as high as 6, or even 10 amps, and the minimum may be about 0.2 or 0.5 amps. The current may be applied after removal of the filter material from the contaminated fluid stream in a separate regenerative operational step. The fluid stream and the fluid flow mass may be a liquid stream and liquid flow mass, respectively.

The electric current may disassociate contaminant without irreversible reduction or irreversible oxidation of the contaminant.

Also described herein is an apparatus for removing contamination from a fluid stream of:

a) a housing containing a filter material comprising carbon and potassium iodide;

b) a fluid inlet port to the housing;

c) a fluid outlet port from the housing;

d) a source of contaminated fluid available to the fluid inlet port;

e) a device for moving fluid through the inlet port and through the outlet port;

f) a direct current source that passes direct current through the filter material; and g) a source of fluid flow mass to move fluid mass over the filter material after or during passage of direct current over the filter material.

Another aspect of technology described herein includes a liquid antimicrobial solution with:

at least 80% of total weight of a carrier liquid comprising water, alcohol or a mixture of water and alcohol or other non-protic solvents;

at least 0.001% by weight of the solution of $K+I^-$;

at least 0.001% by weight of $CuSO_4$; and sufficient acid in the solution top provide a pH of less than 5.0.

The solution may have acid in sufficient amount to provide a pH of from 2.0 to 4.8. The solution has a preferred acid of sulfamic acid.

In the present technology, a carbon filter is activated by intimate, internal association with iodine and/or potassium iodide (KI). This material will be referred to herein as IAC (for Iodine (iodide) activated carbon. Spent or used IAC has an aqueous or alcoholic liquid imbuing or flowing through the spent IAC while a current is passed through the spent IAC within the liquid. The current overcomes the forces binding adsorbed material to the IAC and regenerates the activity in the IAC while the liquid supports and is used to carry away the released formerly filtered and retained materials. As the adsorbed or absorbed materials filtered from either a gaseous or liquid medium are primarily associated with the activated carbon medium (the IAC) through electrical forces, as opposed to covalent bonding, application of current can be highly effective in freeing material bound to the IAC.

The adsorbed contaminants are released from adsorptive binding to the filters and then washed away. This can be done by removal and washing of the filtrate during application of the current, backflushing of the filter bed during application of the current, side flushing (at least one separate flowpath, e.g., a side path, other than the primary inlet and primary outlet paths of fluid flow through the filter bed), or other freed contaminant removal techniques. This system and technology can be used with both gaseous and liquid filtering systems, and can use gaseous removal systems where the freed contaminant is gaseous, or requires a fluid removal system (aqueous or organic or even inorganics such as mineral oil)

depending upon the physical properties of the contaminant in its freed state and the available resources.

One aspect of the present technology is to first load the carbon filters with KI (because the carbon filter along with many other substances in nature possesses an "Iodine number"), e.g., with a water or alcohol solution of KI, and then (continuously) supply DC current across the filter while filtrate passes the assembly, to perform continuous oxidation of organics and metals by free iodine produced from the KI electrolysis described below:

$$I^-_{(aq)} \rightarrow I_{2(s)} + 2e^-$$

$$2H_2O_{(l)} + 2e^- \rightarrow 2OH^-_{(aq)} + H_{2(g)}$$

net reaction: $2I^-_{(aq)} + 2H_2O_{(l)} \rightarrow I_{2(s)} + 2OH^-_{(aq)} + H_{2(g)}$ The filterable fluid then may be passed through the assembly of carbon filter plus electrolysis electrodes, where the free iodine oxidizes the target materials in the medium. This is done with, and without the addition of additional KI upstream. Experimental results produces an obvious layer of brown iodine/KI solution between the electrodes at a separation of 3" between carbon electrodes (in this case) as distinct from the remaining KI solution which remains clear (but contains KI) at nominal DC 6-30 v, 0.08 A.

Similar to the above is the instance where the DC electrolysis energy is replaced by UVC (ultraviolet radiation concentration exposure), typically 253.9-266.0 nm (although within the range of 250-300 nm is particularly useful), but takes longer, and is subject to occlusion by glass and TDS or TSS in the filterable solution.

Gel with Iodine and Boron to Control Radiation Leaks

This aspect of the technology prescribes that the chemical basis of nuclear fuel control rods (boron from boric acid, hafnium, cadmium) be suspended in our CupriDyne-SAP™ gel to a desired consistency without breaking the gel, and then disposing on spent fuel rods, fuel rods, and other nuclear plant containment vessels and areas, to absorb neutrons, and cool down the target. This is useful when water cannot be used, but desirable also in that the flocculent of SAP will acquire the fission products as well, and prevent exposure to alpha, beta, and most gamma rays. Just as firefighting using fire retardant chemicals is dropped from the air, likewise a gel will adhere to all surfaces to cool down the spill or problem rods. In essence, it is a gelled version of a control rod which can be pumped by emergency pumpers. Water with boric acid has been tried by the Japanese, but the amount of boric acid is limited to 3-5%, especially in sea water—not enough to cool down the fuel rods, and then the water leaked out from containment in the particular instance, anyway.

Stable Iodine Liquid Compositions/Solutions (Ready to Use and Concentrate)

An iodine solution is acidified by the addition of an acid that (alone) produces a pH of less than 6.7 at 1.0 N in deionized water and preferably less than 6.5 under those parameters. Typical acids may be organic acids, inorganic acids, Lewis acids, HCl, HI, HBr (halogenic acids), $HNO_3$, $HClO_4$, $H_2SO_4$, $H_2SO_3$, and especially the family of sulfamic acids.

The iodine environment can be provided in numerous and varied tasks and services and even in combination with other additives such as stable active solutions or film-breaking compositions such as acids (e.g., sulfamic acid, hydrochloric acid, sulfuric acid, enzymes, etc.). At present, the most widely known and accepted acidizing agents include HCl, sulfamic acid, lactic acid, citric acid, and acetic acid, all with varying degrees of reactivity for descaling. The effect of acidizing with iodine gas in solution, however, also attends with additive antimicrobial effects, and when the acidized iodine is combined with sulfamic acid, a powerful and effective method is provided for dissolving and remediating biofilms, and chelating heavy metals which may be solubilized by the process, or otherwise contained in water, especially after physical disruption as described herein.

Sulfamic acid is also a primitive surfactant, and when added to free iodine in water and stabilized by varying added compounds such as silicates (e.g., sodium metasilicate) and phosphates and sulfonates (e.g., sodium xylene sulfonate or phosphate), yields a disinfecting and biofilm removing detergent compound which is active within the technologies described herein for oilfield or watershed applications as a single formulary product. The term a "sulfamic acid compound" or a member of the family of sulfamic acids or class of sulfamic acids is herein defined as any sulfamic acid central moiety with a single substituent on the amide group of the sulfamic acid moiety or sulfamic acid core structure that still allows the sulfamic acid derivative in the family of sulfamic acids to display a pH of less than 6.8 at 0.5N in deionized water, preferably less than 6.5 under those parameters (e.g., 5.5 to 6.7, 5.5 to 6.2, and 4.0-6.7, and 3.0 to 6.7 and even lower levels of acidity up to 6.5, up to 6.6 or up to 6.7 pH). As non-limiting examples of these known sulfamic acid family compounds are sulfamic acid, iodosulfamic acid, chlorosulfamic acid, bromosulfamic acid, fluorosulfamic acid, alkylsulfamic acid (with C1-C8 carbon groups, whether linear, branched or cyclic, such as cycloheylsulfamic acid, and substituted or not, such as trifluoromethylsulfamic acid, pentachloroethylsulfamic acid, etc.), cyanosulfamic acid, any electron-withdrawing group on the amide position of the sulfamic acid and even lightly electron-donating groups that do not change the sulfamic acid from an acid to a base at 1.0N in deionized water.

The formula for sulfamic acid is $NH_2SO_3H$ and the corresponding formula for a sulfamic acid compound is represented by:

$NR_2SO_3H$, wherein R is independently selected from the groups described above, such as hydrogen, halogen, cyano, C1-C6 alkyl or substituted alkyl, perhalo alkyl, halosubstituted alkyl, electron-withdrawing groups, mild electron-donating groups and the like. It is preferred that at least one R group is hydrogen.

The inventor has noted that the addition of sulfamic acid (in particular) to all CupriDyne™ treatment composition formulas can provide ultimate stability or even enhanced activity in its various antimicrobial or surface treatment procedures. The sulfamic acid is both an acidifying agent (and other acids may be used) and a primitive surfactant. CupriDyne™ antimicrobial compositions in water is stabilized (free iodine is continuously available) by lowering pH to 5.5-6.7. Even the CuI resulting component is held in solution. The addition of surfactants, such as sodium metasilicate and sodium tripolyphosphate assists in completing a detergent preparation formula. The solutions may have normal levels of iodine therein (e.g., at least 5 ppm or may be concentrated for dilution with greater than 50 ppm, greater than 100 ppm, greater than 200 ppm, up to solubility limits of iodine in aqueous or alcohol solvents.

The solution is preferred where the acid comprises a sulfamic acid compound having the formula:

$NR_2SO_3H$, wherein R is independently selected from the group consisting of hydrogen and electron-withdrawing groups. The acid may comprise a sulfamic acid compound having the formula:

$NR_2SO_3H$, wherein R is independently selected from the group consisting of hydrogen,
halogen, cyano, C1-C6 alkyl, C1 to C6 substituted alkyl, perhalo alkyl, halosubstituted alkyl, and electron-withdrawing groups. The solution may have at least one R is hydrogen in the sulfamic acid compound or only and exactly one R is hydrogen.

These solutions are antimicrobial, have anti-odor effects, and can bleach or remove some stains. The solutions may be applied by direct application of the liquid as a wash, spray, wipe, mist, bath, or provided in a delivery system. The delivery system may be a diffusion, infusion, frangible, desorption, exudation, or other systems. Solid media such as porous foam, slowly soluble solid medium (e.g., alcohol soluble medium carrying dispersed water droplets), thermally openable media (media with pores that may be further opened or expanded to increase outward flow or diffusion of actives, e.g., small pore solid, where pore size increases with heat), a solid composition having soluble solids dispersed therein that can be dissolved o open pores (e.g., NaCl dispersed in polyamide, polyvinylalcohol dispersed in polyolefin, etc.), and the like. Pastes containing high concentrations of the liquid (e.g., cornstarch, PVA, polyvinylpyrollidone, cellulose bases, clay bases, putty, and the like) can be applied to surfaces. Greases or sealants can be applied at joints, seals, areas susceptible to leakage, or placed within environments that may be stable before operating events and need to be activated under use conditions. Simple wettable carriers such as wood chips, saw dust, cellulose fibers, superabsorbent polymers, fabrics, dissolvable pouches, and the like may be positioned within areas where subsequent materials with contaminants are likely to be added during use. The liquid will then be active against microbes and odors and other contaminants.

Example target applications are waste disposal containers, for industrial, medical, residential and commercial fields of utility. Colostomy bags, catheterization collection areas, medical waste disposal boxes or tins, trash cans, garbage cans, bins, containers, litter boxes, and stall bedding are other possible applications. Any tubing or transport carriers may also be treated according to the present technology, by coatings, laminates, flushing, and the like.

The activated carbon may be maintained over an extended period of time by regeneration or partial regeneration of the Iodine Activated Carbon. The contaminants (or materials to be purified) are removed from the fluid medium by the iodine chemically binding, forming a salt with or otherwise temporarily associating with those contaminants. Once a level of contaminant is bound to the IAC (either approaching the end of a batch, diminishing returns on the absorption capability of the IAC, saturation or near saturation of the IAC, a commercially useful level of bound material that is to be collected, and the like), the filtration process is halted. The medium flowing through the IAC bedding or column is then changed to a cleaner medium, such as water, alcohol, light organic liquids and/or mixtures thereof. Current, preferably direct current is passed through the loaded IAC while the fresh, clean medium is maintained in a batch operation or in a continuous operation. The applied current is varied by considering the relative strengths of the I-contaminant bond strength, the I-carbon bond strength, density of contaminants in the IAC, concentration of the dissociated contaminant in the fluid medium, flow rate of the medium across the loaded IAC and the like. For example, with a low I-contaminant bond strength and relatively higher I-carbon bond strength, low to intermediate currents may be used in a batch or continuous process. As the difference in relative bond strengths narrows, higher currents are desirable, along with slower medium flow over the loaded IAC.

Other variations within the generic scope of the invention can be designed by users to marginally improve or optimize the performance of the present invention and remain within the scope of the claims. Variations in concentrations, flow rates, volumes, current and other controllable parameters are within the skill of the ordinary artisan.

What is claimed:

1. A method of filtering contaminants from a fluid stream comprising: providing a filter material comprising both potassium iodide and activated carbon; passing a contaminated fluid stream in contact with the filter material; adsorbing contaminants from the fluid stream onto the filter material; passing an electric current through the filter material with adsorbed contaminant thereon; disassociating contaminant from the filter material; and removing disassociated contaminant from the filter material by carrying away the disassociated contaminant in a fluid flow mass.

2. The method of claim 1 wherein the filter material comprises activated carbon and at least 0.05% by total weight of solids of iodide salt.

3. The method of claim 2 wherein the iodide salt comprises potassium iodide intimately mixed throughout the activated carbon.

4. The method of claim 2 wherein the iodide salt comprises potassium iodide is distributed on at least some surfaces of the activated carbon.

5. The method of claim 4 wherein the electric current is applied at voltages between 2.0 and 15 volts.

6. The method of claim 5 wherein the current is applied after removal of the filter material from the contaminated fluid stream.

7. The method of claim 5 wherein the fluid stream and the fluid flow mass comprises a liquid stream and liquid flow mass, respectively.

8. The method of claim 1 wherein the electric current disassociates contaminant without irreversible reduction or irreversible oxidation of the contaminant.

9. The method of claim 1 wherein after dissociation of the contaminant, the carbon is thermally regenerated.

10. The method of claim 9 wherein thermal regeneration is effected by a procedure comprising three steps:
    a) adsorbent drying;
    b) desorption and decomposition at between 500-900° C. under an inert atmosphere; and
    c) residual organic gasification by an oxidizing gas at elevated temperatures.

11. The method of claim 10 wherein the oxidizing gas comprises steam or carbon dioxide.

12. The method of claim 1 wherein the stream comprises a waste water stream.

13. The method of claim 1 wherein the activated carbon is activated by intimate, internal association with iodine and/or potassium iodide (KI).

14. The method of claim 1 wherein the filter material consists essentially of activated carbon and KI and the activated carbon is activated by intimate, internal association with iodine and/or potassium iodide (KI).

15. The method of claim 8 wherein the filter material consists essentially of activated carbon and KI and the activated carbon is activated by intimate, internal association with iodine and/or potassium iodide (KI).

16. The method of claim 1 wherein the KI is present on the activated carbon as solution deposited KI.

* * * * *